United States Patent
Ujhazy et al.

(10) Patent No.: US 10,856,802 B2
(45) Date of Patent: Dec. 8, 2020

(54) METHODS AND APPARATUS FOR HEART FAILURE TREATMENT

(71) Applicant: ResMed Pty Ltd, Bella Vista (AU)

(72) Inventors: Anthony John Ujhazy, Sydney (AU); Jonathan Caldwell Wright, Sydney (AU); Glenn Richards, Auckland (NZ); David John Bassin, Sydney (AU); Michael Berthon-Jones, Sydney (AU)

(73) Assignee: ResMed Pty Ltd

( * ) Notice: Subject to any disclaimer, the term of this patent is extended or adjusted under 35 U.S.C. 154(b) by 584 days.

(21) Appl. No.: 15/017,790

(22) Filed: Feb. 8, 2016

(65) Prior Publication Data

US 2016/0151014 A1    Jun. 2, 2016

Related U.S. Application Data

(63) Continuation of application No. 13/718,084, filed on Dec. 18, 2012, now Pat. No. 9,283,341, which is a
(Continued)

(51) Int. Cl.
*A61B 5/00* (2006.01)
*A61M 16/00* (2006.01)
(Continued)

(52) U.S. Cl.
CPC ............ *A61B 5/4836* (2013.01); *A61B 5/087* (2013.01); *A61B 5/0826* (2013.01);
(Continued)

(58) Field of Classification Search
CPC ..... A61B 5/4836; A61B 5/0826; A61B 5/087; A61M 16/0069
See application file for complete search history.

(56) References Cited

U.S. PATENT DOCUMENTS

| | | |
|---|---|---|
| 4,519,399 A | 5/1985 | Hori |
| 4,944,310 A | 7/1990 | Sullivan |
| | (Continued) | |

FOREIGN PATENT DOCUMENTS

| | | |
|---|---|---|
| EP | 1295623 A1 | 3/2003 |
| GB | 2294642 A | 5/1996 |
| | (Continued) | |

OTHER PUBLICATIONS

EPO Supplementary Search Report for co-pending application No. 04789586.7; dated Jul. 22, 20010.
(Continued)

*Primary Examiner* — Scott M. Getzow
(74) *Attorney, Agent, or Firm* — Botos Churchill IP Law LLP

(57) ABSTRACT

Methods and apparatus for assessing the condition of and treating patients for heart failure by the delivery of continuous positive airway pressure are disclosed. Treatment of obstruction due to reflex vocal cord closure often experienced by heart failure patients is distinguished from treatment of upper airway obstruction typically associated with Obstructive Sleep Disorder. Treatment may also be implemented by delivering synchronized cardiac pressure oscillations superimposed on a respiratory pressure level to provide assistance for the heart. Heart treatment pressure dose indicator may be calculated for prescribing and monitoring the delivery of treatment. The apparatus may also generate data to track heart failure condition that may be indicative of the degree of severity of heart failure based upon breathing patterns to assist in the diagnosis and management of heart failure patients.

52 Claims, 13 Drawing Sheets

Related U.S. Application Data continuation of application No. 12/613,035, filed on Nov. 5, 2009, now Pat. No. 8,356,594, which is a continuation of application No. 10/575,197, filed as application No. PCT/AU2004/001420 on Oct. 15, 2004, now abandoned.

(60) Provisional application No. 60/512,553, filed on Oct. 17, 2003.

(51) Int. Cl.
    *A61M 16/06*     (2006.01)
    *A61B 5/08*     (2006.01)
    *A61B 5/087*     (2006.01)

(52) U.S. Cl.
    CPC ............ *A61B 5/7282* (2013.01); *A61B 5/746* (2013.01); *A61M 16/0051* (2013.01); *A61M 16/0057* (2013.01); *A61M 16/0066* (2013.01); *A61M 16/0069* (2014.02); *A61M 16/06* (2013.01); *A61M 2016/0021* (2013.01); *A61M 2016/0036* (2013.01); *A61M 2205/3344* (2013.01); *A61M 2230/005* (2013.01); *A61M 2230/04* (2013.01); *A61M 2230/10* (2013.01); *A61M 2230/18* (2013.01); *A61M 2230/40* (2013.01); *A61M 2230/435* (2013.01); *A61M 2230/63* (2013.01)

(56) References Cited

U.S. PATENT DOCUMENTS

| | | | |
|---|---|---|---|
| 5,020,516 A | 6/1991 | Biondi et al. | |
| 5,188,098 A | 2/1993 | Hoffman et al. | |
| 5,353,788 A | 10/1994 | Miles | |
| 5,535,738 A | 7/1996 | Estes et al. | |
| 5,584,290 A | 12/1996 | Brain | |
| 5,625,723 A | 4/1997 | Dragone et al. | |
| 5,704,345 A | 1/1998 | Berthon-Jones | |
| 5,740,797 A | 4/1998 | Dickson | |
| 5,794,615 A | 8/1998 | Estes | |
| 5,846,720 A | 12/1998 | Foulkes et al. | |
| 6,105,575 A | 8/2000 | Estes et al. | |
| 6,120,442 A | 9/2000 | Hickey | |
| 6,152,129 A | 11/2000 | Berthon-Jones | |
| 6,454,719 B1 | 9/2002 | Greenhut | |
| 6,532,957 B2 | 3/2003 | Berthon-Jones | |
| 6,532,959 B1 | 3/2003 | Berthon-Jones | |
| 7,413,549 B1 | 8/2008 | Koh | |
| 7,787,946 B2 | 8/2010 | Stahmann et al. | |
| 2002/0088465 A1 | 7/2002 | Hill | |
| 2002/0169384 A1 | 11/2002 | Kowallik et al. | |
| 2003/0078619 A1 | 4/2003 | Bonnet et al. | |
| 2003/0121519 A1 | 7/2003 | Estes et al. | |
| 2003/0154979 A1 | 8/2003 | Berthon-Jones | |
| 2004/0134496 A1 | 7/2004 | Cho et al. | |
| 2004/0237963 A1 | 12/2004 | Berthon-Jones | |
| 2005/0080348 A1 | 4/2005 | Stahmann et al. | |
| 2007/0142741 A1 | 6/2007 | Berthon-Jones et al. | |

FOREIGN PATENT DOCUMENTS

| | | |
|---|---|---|
| WO | 8909041 A1 | 10/1989 |
| WO | 9730744 A1 | 8/1997 |
| WO | 1998012965 A1 | 4/1998 |
| WO | 99/45989 A1 | 9/1999 |
| WO | 99/61088 A1 | 12/1999 |
| WO | 00-45702 A1 | 8/2000 |
| WO | PCT/DK00/00040 | 8/2000 |
| WO | 0067827 A1 | 11/2000 |
| WO | 01/19433 A1 | 3/2001 |
| WO | 2002/026283 A2 | 4/2002 |
| WO | 2005/018737 A1 | 3/2005 |

OTHER PUBLICATIONS

Extended European Search Report for Application No. EP12153548 dated Dec. 20, 2013.
International Search Report for Application No. PCT/AU2004/001420 dated Jan. 12, 2005.
U.S. Appl. No. 12/757,130, filed Apr. 9, 2010.
US Office Action for U.S. Appl. No. 12/757,130 dated Feb. 25, 2013.
US Office Action for U.S. Appl. No. 12/757,130 dated Jun. 20, 2013.

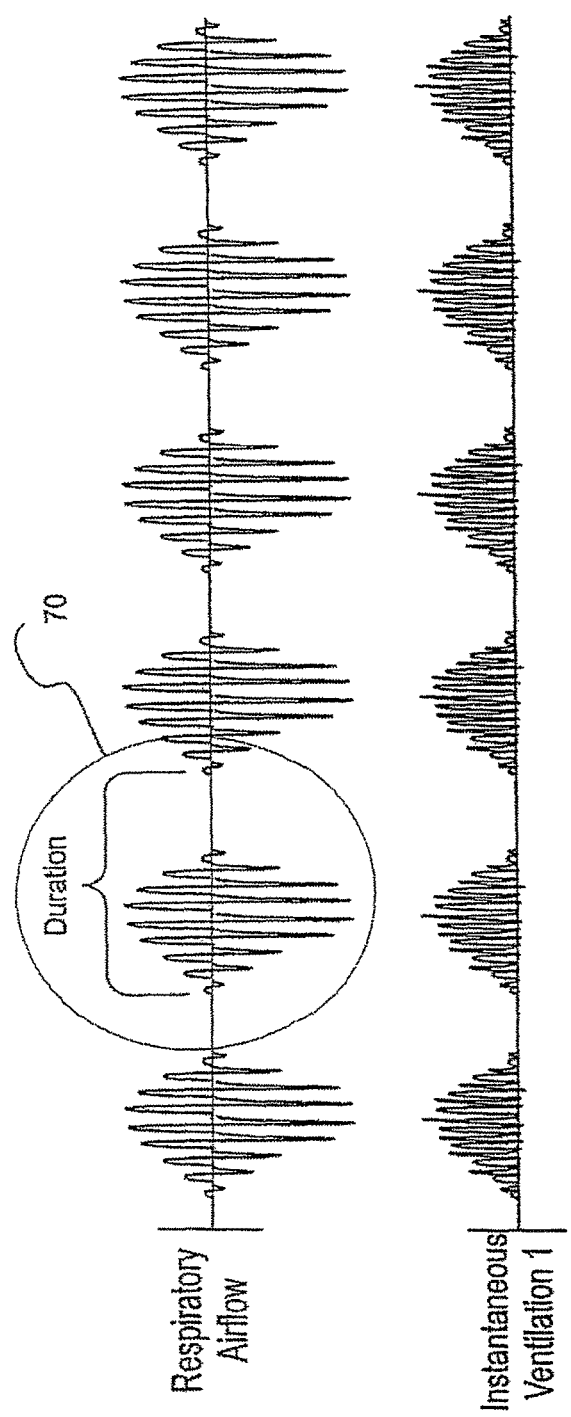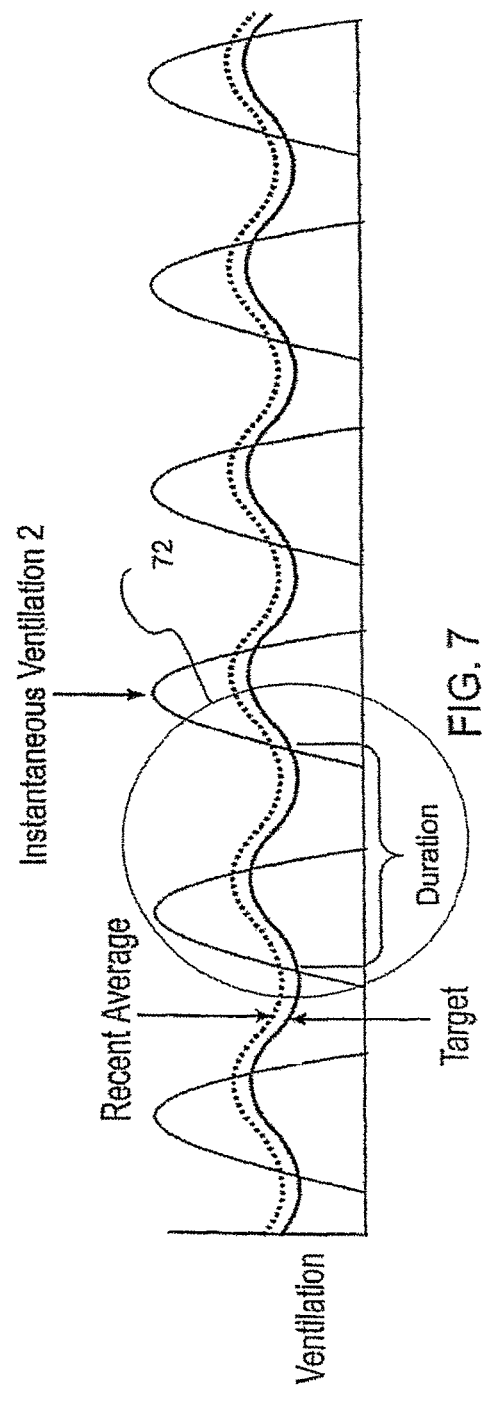
FIG. 7

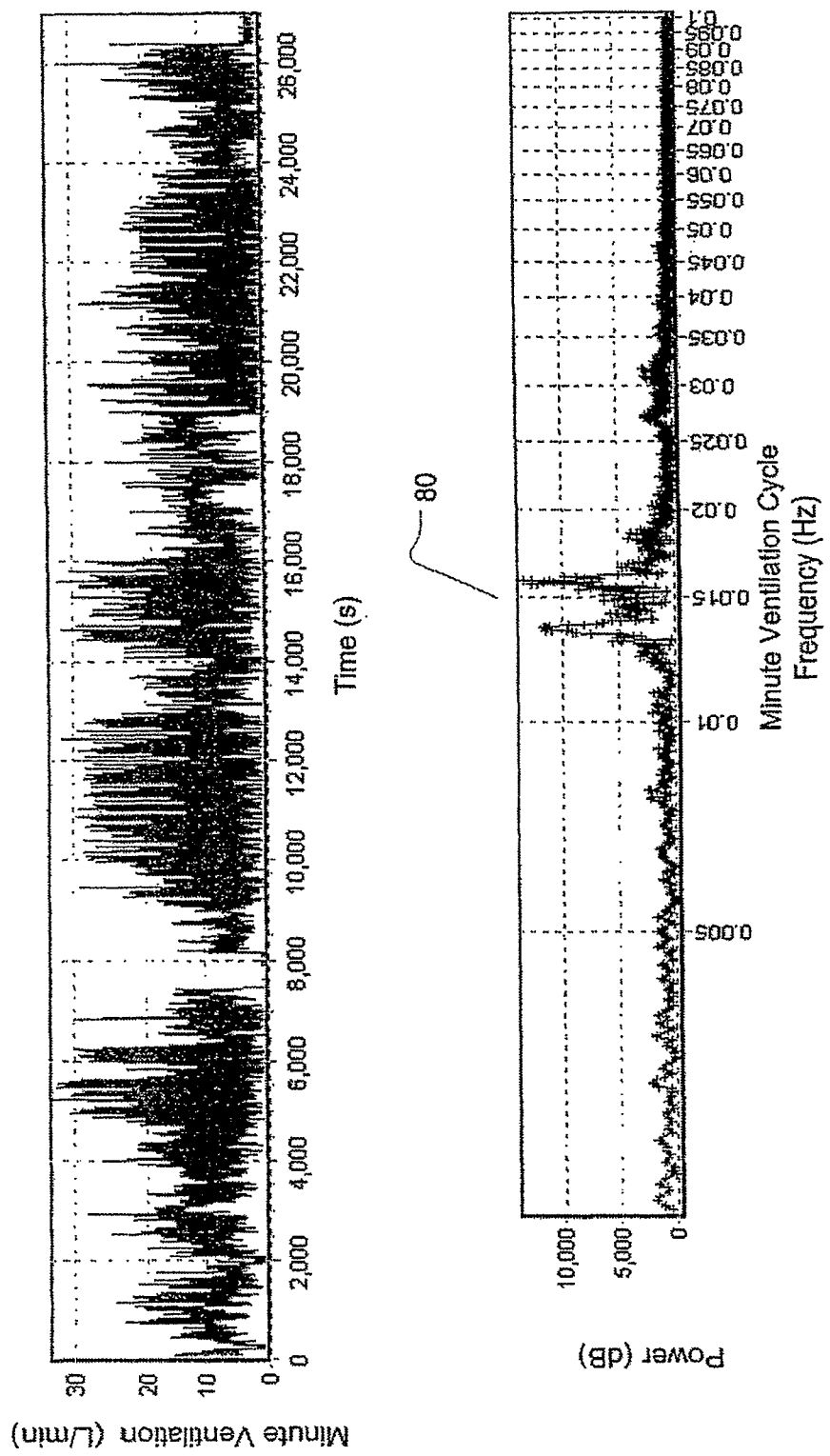

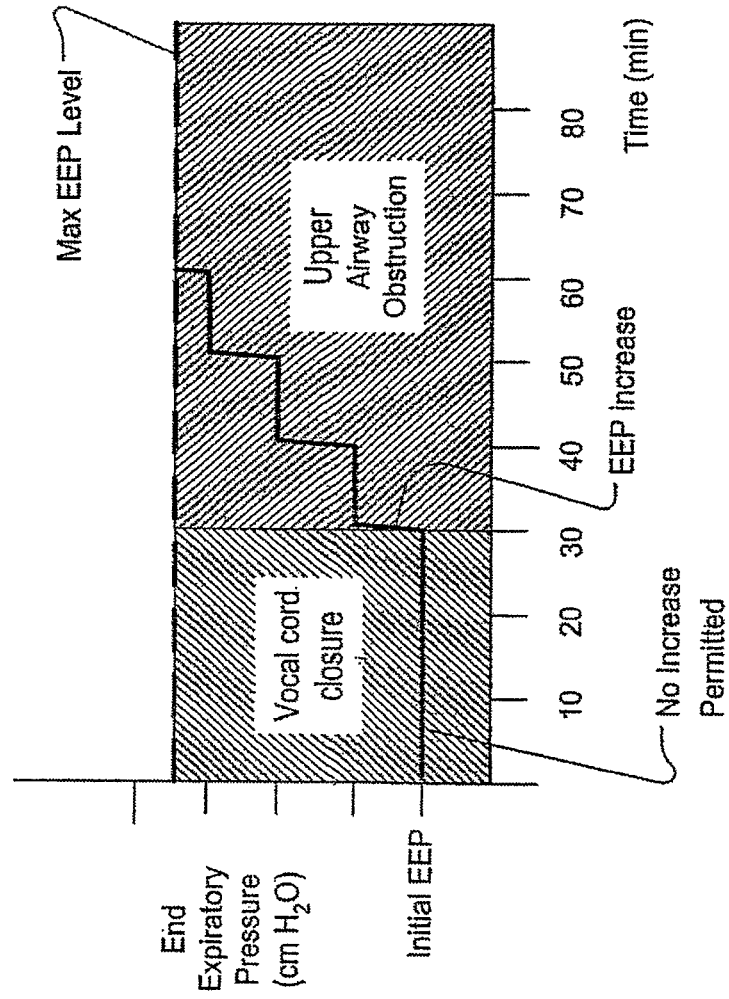

METHODS AND APPARATUS FOR HEART FAILURE TREATMENT

CROSS-REFERENCE TO RELATED APPLICATIONS

The present application is a continuation of Ser. No. 13/718,084, filed Dec. 18, 2012, which is a continuation of U.S. patent application Ser. No. 12/613,035, filed Nov. 5, 2009, now U.S. Pat. No. 8,356,594, which is a continuation of U.S. patent application Ser. No. 10/575,197, filed Jul. 31, 2006, which is a continuation of International Application No. PCT/AU04/01420, filed Oct. 15, 2004, which claims the benefit of the filing date of U.S. Provisional Patent Application No. 60/512,553, filed on Oct. 17, 2003, all of which are hereby incorporated herein by reference.

FIELD OF THE INVENTION

The invention relates to methods and apparatus for diagnosing, managing and treating congestive heart failure.

BACKGROUND OF THE INVENTION

It has been estimated that in the United States alone that almost five million people suffer from congestive heart failure. Statistics from the American Heart Association also suggest that new cases of heart failure are diagnosed at a rate of about 500,000 each year. Of the newly diagnosed patients fifty percent are likely to die within five years from the initial diagnosis. Of course, these numbers do not account for the number of patients in other countries who also suffer from heart failure. Given these numbers, it is clear that congestive heart failure is a significant human crisis.

Heart failure is a condition that is characterized by a reduced ability of the heart to circulate blood through the body. Typically, an underlying disease, such as high blood pressure (e.g., hypertension), clogged arteries (e.g., coronary artery disease), heart defect (e.g., cardiomyopathy, or valvular heart disease) or some other problem (e.g., diabetes, hyperthyroidism, or alcohol abuse) will lead to a decrease in circulation over time. As the heart works less efficiently, its capacity to circulate blood decreases and the body's requirements for oxygen are not met. The cardiac muscle tends to enlarge as the heart works harder over time to compensate for the decrease in efficiency.

Heart failure may be identified by the phase of the heart cycle that is particularly associated with the nature of the circulatory problem. By this identification, two types of heart failure are known as systolic and diastolic. In systolic heart failure, the cardiac muscles' ability to contract decreases. This loss of contraction results in a decrease in the ability of the heart to force blood through the circulatory system of the body. In diastolic heart failure, the cardiac muscles' ability to relax diminishes. As the heart muscles become stiffer, the heart does not sufficiently fill with blood and thus each subsequent contraction circulates a lower volume of blood.

Alternatively, heart failure may be characterized by whether it stems from problems with the left or right side of the heart. Left-sided heart failure occurs when the left ventricle does not sufficiently pump oxygenated blood to the body. Right-sided heart failure occurs when the right ventricle does not pump adequately, which leads to fluid build-up in the veins.

Although the phrase "congestive heart failure" is often used to describe all types of heart failure including the above listed types, congestive heart failure is more accurately descriptive of a symptom of heart failure relating to pulmonary congestion or fluid buildup in the lungs. This congestion is more commonly symptom of systolic and left-sided heart failure. As the efficiency of the pulmonary system declines, increased blood volume near the input side of the heart changes the pressure at the alveolar arterial interface, an interface between the lung capillaries and the alveolar space of the lungs. The change in pressure at the interface causes blood plasma to push out into the alveolar space in the lungs. Shortness of breath ("dyspnea") and general fatigue are typical perceived manifestations of congestive heart failure.

Congestive heart failure ("CHF") is currently classified by severity. Class I patients have no apparent symptoms and no physical activity limitations. Class II patients experience some symptoms during moderate to severe physical activity. Class III patients suffer symptoms at mild levels of physical activity. Class IV patients experience symptoms with any form of physical activity as well as at rest.

While the only cure to CHF is heart transplant, there are a number of drug and surgical treatments directed at reducing the underlying problem that led to the heart failure and/or to alleviate the symptoms of heart failure. For example, the use of diaretics is intended to reduce congestion by depleting the body of fluids. Vasodilators such as ACE inhibitors are used to expand blood vessels and reduce resistance to blood circulation. Beta blockers seek to reduce the work load on the heart by normalizing the rhythm of the heart. Cardiotonic drugs are directed at increasing the force of the heart's contractions. Surgical procedures include physical manipulation in an attempt to increase the internal size of constricted arteries, for example, by balloon angioplasty or stenting.

As previously noted, as a consequence of heart failure there is a decreased flow of oxygen in the circulatory system. This decease in oxygenated blood through the body has an impact on the body's respiratory controller. Thus, there appears to be a relationship between congestive heart failure and respiratory conditions known as Sleep Disordered Breathing ("SDB"). For example, it has been noted that 50-60% of heart failure patients have SDB. In this category of patients, approximately 29% may be classified as suffering from obstructive sleep apnea, a breathing condition associated with the cessation or limitation of airflow due to occlusion usually at the level of the tongue or soft palate. In addition, 33% of the patients maybe classified as suffering from (a) Cheyne-Stokes respiration, a breathing condition characterized by waxing and waning breathing patterns or (b) central sleep apnea, a condition involving a cessation of airflow due to a cessation of patient respiratory effort. For those patients suffering from Cheyne-Stokes breathing, there is a greater degree of concern. These patients have a higher mortality rate then heart failure patients without Cheyne-Stokes breathing.

Sleep disordered breathing has long been treated by application of Continuous Positive Airway Pressure ("CPAP"). CPAP was invented by Sullivan and taught in U.S. Pat. No. 4,944,310. That patent describes continuous positive airway pressure being applied to a patient, through the patient's nares, to treat breathing disorders, including obstructive sleep apnea. It has been found that the application of pressure which exceeds atmospheric pressure, typically in the range 4 to 15 centimeters of $H_2O$, is useful in treatment. The pressure acts as a pneumatic splint to maintain upper airway patency to ensure free flow of air while the patient sleeps.

In one form, nasal CPAP treatment of Obstructive Sleep Apnea ("OSA") involves the use of an automated blower, such as the AUTOSET T™ device or AUTOSET SPIRIT™ available from ResMed Ltd., to provide a constant supply of air or breathable gas at pressures in the range of 4 to 20 cm $H_2O$ to the airway of a patient via a mask. Examples of suitable nasal CPAP masks are the MIRAGE™ nasal mask and the MIRAGE™ full face mask also available from ResMed Ltd. The AUTOSET T™ device continuously monitors the state of the patient's airway and determines an appropriate pressure to treat the patient, increasing it or decreasing it as necessary. Alternatively, bilevel pressures are delivered to the patient as in the VPAP II™ devices also available from ResMed Ltd. Some of the principles behind the operation of the AUTOSET T™ and VPAP II™ devices are described in U.S. Pat. No. 5,704,345. The entire disclosure of U.S. Pat. No. 5,704,345 is incorporated herein by reference.

One form of pressure treatment is delivered in accordance with a smooth pressure waveform template and a continuous phase variable to provide comfortable pressure support substantially in phase with the patient's respiratory cycle. The device is the subject of International Publication No. WO 98/12965. The device is also the subject of U.S. patent application Ser. No. 08/935,785, now U.S. Pat. No. 6,532,957, the entire disclosure of which is hereby incorporated by reference.

Another form of pressure treatment is directed at treatment of Cheyne-Stokes breathing. In a device designated AUTOSET CS™, also provided by ResMed Ltd., pressure support is varied in phase with patient respiration in such a manner to oppose the waxing and waning changes in patient respiration that characterize Cheyne-Stokes breathing. The device is the subject of International Publication No. WO 99/61088. The device is also the subject of a U.S. patent application Ser. No. 09/316,432, now U.S. Pat. No. 6,532,959, the entire disclosure of which is incorporated herein by reference.

At present, there are no known devices with features designed to treat a range of symptoms of heart failure patients through application of pressure as opposed to devices that might only incidentally provide such benefits. U.S. Pat. No. 5,794,615 teaches a device to provide a level of pressure support to reduce cardiac pre-load and after load. However, the device is only taught to provide one continuous level of pressure during inspiration and another level during expiration. The patent does not suggest the provision of a waveform of cardiac pressure oscillations in phase with a patient's cardiac rhythm, a feature of the present invention as described below. Moreover, the device provides no assistance directed to alleviating Cheyne-Stokes breathing or distinguishing between obstructions due to vocal cord reflex and obstructions from typical OSA due to collapse of the upper airway during sleep.

Any reference herein to known prior art does not, unless the contrary indication appears, constitute an admission that such prior art is commonly known by those skilled in the art to which the invention relates, at the priority date of this application.

BRIEF SUMMARY OF THE INVENTION

It is an objective of the invention to provide methods and apparatus for managing the treatment of respiratory disorders in congestive heart failure patients.

It is a further objective to provide methods and apparatus that assist in the identification or diagnosis of heart failure to assist with treatment of the patient.

Other objectives will be apparent to those skilled in the art from a review of the description of the invention as contained herein.

The invention provides methods and apparatus for detecting reflex vocal cord closure. The vocal cord closure detector derives a measure indicative of the closure. Preferably, the measure is indicative of a state of sleep and may be derived from respiratory airflow of the patient as a function of a minute ventilation and an elapsed time. The delivery of positive airway pressure treatment is controlled as a function of the measure. In the preferred embodiment of the invention, any apnea or obstructive event detected before about 30 minutes of sleep is determined to be vocal cord closure and treatment levels are not increased. Apneas detected after these thresholds are met and treated as a non-vocal cord obstructive apnea by an increase in pressure. Alternatively, reflex vocal cord closure may be detected by distinguishing an incident of vocal cord closure from another type of airway obstruction based on a derived measure indicative of vocal cord closure. The step of distinguishing may include detecting an obstructive event and conditioning an increase in treatment pressure in response to the detected obstructive event by an analysis of the derived measure of the closure. This analysis may include a comparison of the derived measure with a time limit of about 30 minutes. The invention further includes methods and apparatus for providing a synchronized cardiac waveform to perform some work of the cardiac organ. The cardiac waveform may be a square wave or sinusoidal wave in phase with detected cardiac rhythm and is preferably superimposed with continuous, hi-level or other oscillatory respiratory treatment pressure that supports the patient's respiration or maintains an open airway. The cardiac waveform is preferably delivered with amplitudes in a range of approximately 1 to 2 cm $H_2O$.

The invention also includes a means for calculating a heart treatment index to regulate or measure the dose of treatment to the heart from the synchronized oscillations. The measure determines the index as a function of duration and delivered pressure and preferably accounts only for time that the treatment oscillations are actually delivered to the thorax by excluding treatment during closed airway apnea or periods of high leak. In one embodiment of the invention, the index is the product of an average pressure and the duration of treatment.

Finally, the invention includes methods and apparatus for assessing heart failure in a patient by calculation or determination of a heart failure indicator or index. Such an indicator may be determined from respiratory airflow by assessing an extent of Cheyne-Stokes breathing in the patient. Alternative embodiments of the indicator include measures of the duration of waxing and waning cycles or frequency analysis of components of a measure of airflow in a range of frequencies associated with Cheyne-Stokes breathing. In addition, an appropriate indicator may be a measure of minute ventilation compared with a threshold of about 15 L/min. or alternatively a ratio of a minimum and maximum of a measure of ventilation, such as a minute ventilation or a tidal volume. Changes in such indicators taken by comparing or analyzing indicators from a current session with assigned thresholds or predetermined threshold values including indicators from prior sessions provide a diagnostic tool for assessing improvement or deterioration of the patient's condition.

BRIEF DESCRIPTION OF THE DRAWINGS

An embodiment or embodiments of the present invention will now be described, by way of example only, with reference to the accompanying drawings, in which:

FIG. 7 depicts several graphs relating to detection of Cheyne-Stokes breathing in a patient;

FIG. 8A depicts a graph of minute ventilation determined from a flow signal from a patient experiencing Cheyne Stokes breathing and a graph of a frequency spectrum of the minute ventilation;

FIG. 9 illustrates a treatment protocol for distinguishing between vocal cord closure and upper airway obstruction;

DETAILED DESCRIPTION

Figure 1:
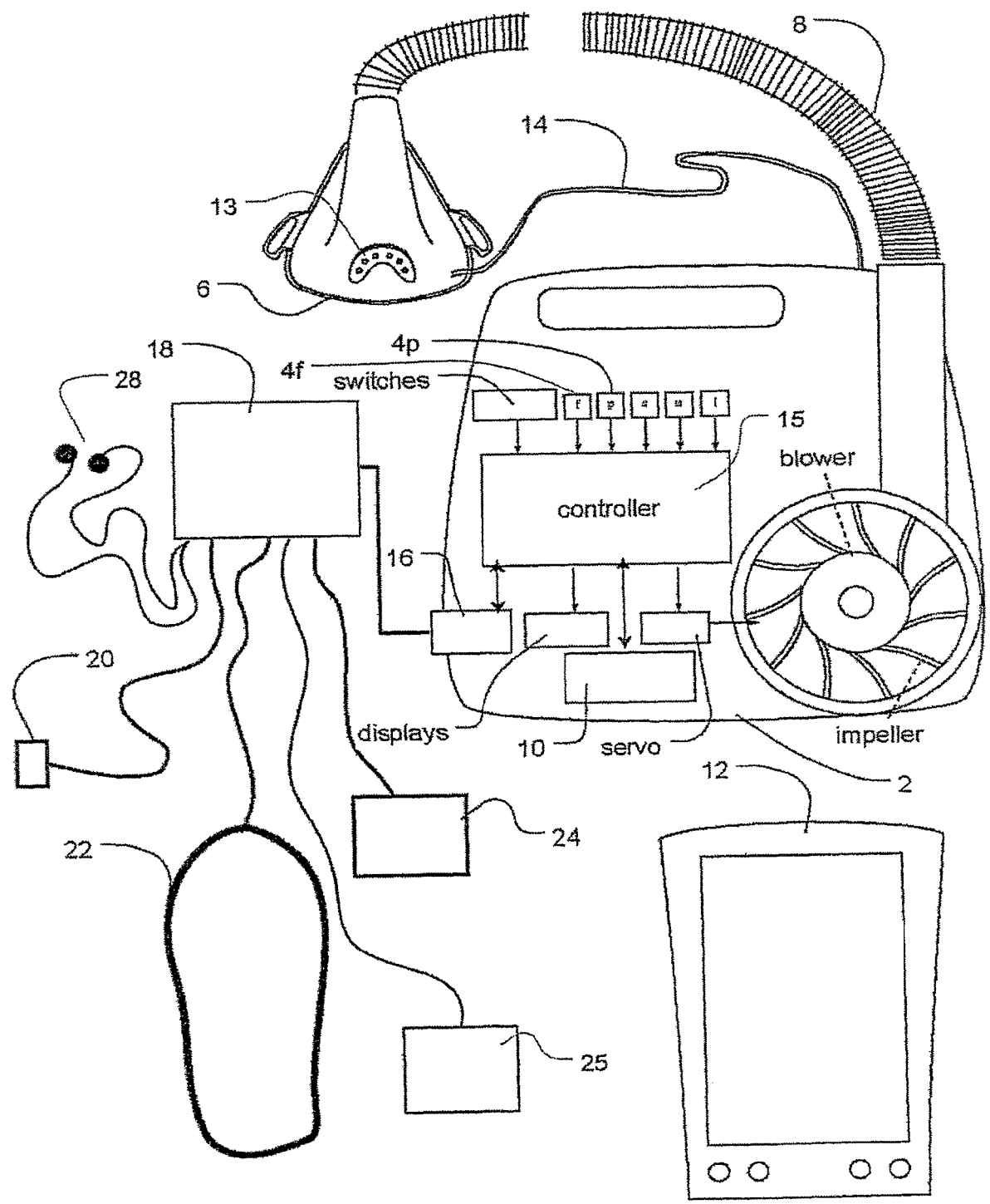
FIG. 1 shows apparatus according to the invention.

In reference to FIG. 1, the heart failure treatment invention involves an apparatus that includes a blower 2, a flow sensor 4f, pressure sensor 4p, a mask 6, and an air delivery conduit 8 for connection between the blower 2 and the mask 6. Exhaust gas is vented via exhaust 13. Mask flow is preferably measured using a pneumotachograph and differential pressure transducer to derive a flow signal F(t). Mask pressure is preferably measured at a pressure tap using a pressure transducer to derive a pressure signal Pmask(t). The pressure sensor 4f and flow sensor 4p have only been shown symbolically in FIG. 1 since it is understood that those skilled in the art would understand how to measure flow and pressure. Flow F(t) and pressure Pmask(t) signals are sent to a controller or microprocessor 15 to derive a pressure request signal PRequest(t). The controller or processor is configured to implement the methodology described in more detail herein and may include integrated chips, a memory and/or other instruction or data storage medium. Programmed instructions may be either coded on integrated chips in the memory of the device or may be loaded as software.

The apparatus further includes a communication port or module 10, for example, a wireless communication transceiver and/or a network card, for communication with other devices or computers such as hand-held display and control devices 12. The apparatus optionally includes an oximeter in the main blower housing. There is a sense tube 14 connected to the main housing of the blower to the mask that allows the apparatus to sense oxygen concentration and pressure levels in the mask 6. The apparatus may further include additional communications interface 16 for connection to additional diagnosis devices. The diagnosis unit optionally includes a pulse oximeter 20, respiratory movement sensors 22, EEG & ECG 24 and/or EOG 25. The unit may also include a set of electrodes 28 for detecting cardiac rhythm.

While this apparatus is described as a single unit, it is understood that a combination of devices and/or computers linked by any available communications method may be used to accomplish the goals of the invention. For example, the apparatus can interface with a variety of hand-held devices such as a Palm Pilot via wireless communication. With such a device, a physician may, for example, remotely monitor, analyze or record the status or data history of a patient or diagnose the severity of the patient's condition using the device. For example, remote devices may store heart failure indicators, such as in a database of patient heart failure recovery information for one or more patients, from data generated by use of the apparatus. Furthermore, the treatment program that is being run on the patient can be monitored and changed remotely. In the event patient data is transmitted over open networks, the data may be encrypted for purposes of patient confidentiality.

The apparatus incorporates various treatment protocols. One protocol is intended for treating obstructive apneas. Another is for treating central apneas. An additional protocol is for treating Cheyne-Stokes breathing. As described in more detail below, the apparatus determines treatment automatically.

In one mode, the device provides a generally constant pressure throughout a breathing cycle, but may vary the pressure in accordance with indications of partial or complete obstruction of the airway. One technique for accomplishing this using a combination of flow limitation and snore measurements is described in U.S. Pat. No. 5,704,345 (Berthon-Jones). Other known alternative methods to vary the pressure for delivering CPAP treatment to a patient to treat obstructive apneas would be recognized by those skilled in the art and may be utilized as operating modes in the device.

In another mode, the apparatus provides a higher pressure to the mask during the inspiratory portion of the breathing cycle, a so-called IPAP (inspiratory positive airway pressure), and a lower pressure to the mask during the expiratory portion of the breathing cycle, a so-called EPAP (expiratory positive airway pressure). This may be accomplished by monitoring the respiratory flow to the patient and defining threshold levels to distinguish between inspiration and expiration. When flow exceeds a threshold then the device delivers IPAP. Below a threshold, the device delivers EPAP.

Alternatively, the treatment delivered by the apparatus will smoothly vary in accordance with patient respiration to provide a smooth pressure waveform. For example, the device calculates a continuous phase variable to provide support in phase with the patient's breathing cycle and calculates the pressure to be delivered in accordance with a pressure waveform template. The delivery of such pressure is disclosed in U.S. patent application Ser. No. 08/935,785. Alternatively, pressure may be supplied in proportion to patient respiratory airflow.

In another form, pressure support is varied in phase with patient respiration in such a manner to oppose the waxing and waning changes in patient respiration that characterize Cheyne-Stokes breathing. The methodology for such treatment is disclosed in U.S. patent application Ser. No. 09/316,432.

While the blower 2 may alternately generate different pressure levels in accordance with the varying pressure delivery methods just described, in an alternative version, a near-constant speed of blower 2 can be maintained and the pressure drops are achieved by venting with the inclusion of a controllable release valve. The same apparatus can be used for many different therapies simply by adjusting the equation that is used to set the speed of the blower or to manipulate the venting with the release valve.

In providing these treatment methodologies, an accurate determination of respiratory airflow is important. Thus, the flow rate of air to the patient is adjusted to account for the effect of leak. To this end, leak airflow may be determined by using a method such as taught in U.S. Pat. No. 6,152,129 (Berthon-Jones), the entire disclosure of which is incorporated herein by reference. Other known methods for determining leak may also be used by the device.

With such a device, positive pressure ventilation can be applied in the treatment of heart failure patients as further described herein. Positive pressure addresses the symptoms of heart failure patients by (a) providing increased airflow to assist in drying fluid from the lungs; (b) reducing fluid transfer to the lungs by increasing the pressure in the alveolar space to offset the pressure differential across the alveolar arterial interface; (c) performing some work of the heart to assist with circulation by reducing the size of the heart to allow the heart to operate more efficiently as a result of increased pressure in the thoracic cavity adjacent to the heart or by providing a contracting assistance or oscillating force in the thoracic cavity; (d) supporting respiration to provide ventilatory assistance that compensates or prevents the waxing and waning cycles associated with Cheyne-Stokes breathing while also providing support to prevent or treat obstructive events; and (e) performs some portion of the work of breathing. Further objectives will be apparent to those skilled in the art based upon the disclosure herein.

A. Reflex Vocal Cord Closure Detection

One of the complexities of the design of the operation of such a device relates to the nature of the breathing difficulties experienced by CHF patients. As previously noted, CHF patients are likely to experience Cheyne-Stokes breathing, central apneas and/or obstructive events. However, the treatment protocol for each may be distinct. Therefore, a device of the invention is configured to automate a change of the treatment protocol based upon the likelihood of the occurrence of the various respiratory and airway abnormalities particularly associated with heart failure patients.

To this end, it has been observed that CHF patients may experience Cheyne-Stokes breathing while a patient is awake. Patients may also experience Cheyne-Stokes breathing or central apneas in earlier stages of sleep particularly stage 1 and stage 2 sleep but not typically during REM sleep. Patients also experience obstructive apneas due to upper airway collapse. Such collapse is typically a result of the relaxed state of the patient induced by sleep. Therefore, these obstructive apneas may occur during the latter stages of sleep and are more likely to occur during REM sleep.

Methods for the detection of obstructive apnea, airway obstruction and central apnea are disclosed in detail in U.S. Pat. No. 5,704,345 and are otherwise known in the art. Obstructive events may be determined by analysis of patient flow to determine shape factors, flow flattening indices, roundness indices, etc. Moreover, with a detected apnea, (e.g., a calculated variance falling below a threshold value) it can be determined whether the apnea constitutes airway obstruction or an absence of respiratory effort (i.e., central apnea). In one such technique, when an apnea is detected as occurring, the apparatus applies an oscillatory pressure waveform of known frequency and magnitude and assesses the patency of the airway from the flow that is induced in the airway. In one form, if the airway is patent during an apnea, then the apnea is judged to be central. However, if the airway is closed during an apnea, then the apnea is judged to be obstructive. In another technique, when an apnea is detected as occurring, the apparatus monitors the airflow for the presence of a signal of cardiac origin. If a cardiac signal is detected, then the airway is judged to be patent and the apnea classified as central. If no cardiac signal is detected, then the airway is judged to be closed and the apnea classified as obstructive.

Other methods for distinguishing between central and obstructive apneas include monitoring chest movement to detect physical respiratory effort using respiratory bands or monitoring the movement of the suprasternal notch, for example, as taught in International Patent Application WO 01/19433 (Berthon-Jones et al.), also taught in U.S. patent application Ser. No. 08/396,031, the disclosure of which is hereby incorporated by reference. When there is no respiratory effort when an apnea is detected, it may be considered a central apnea rather than obstructive.

Figure 10:
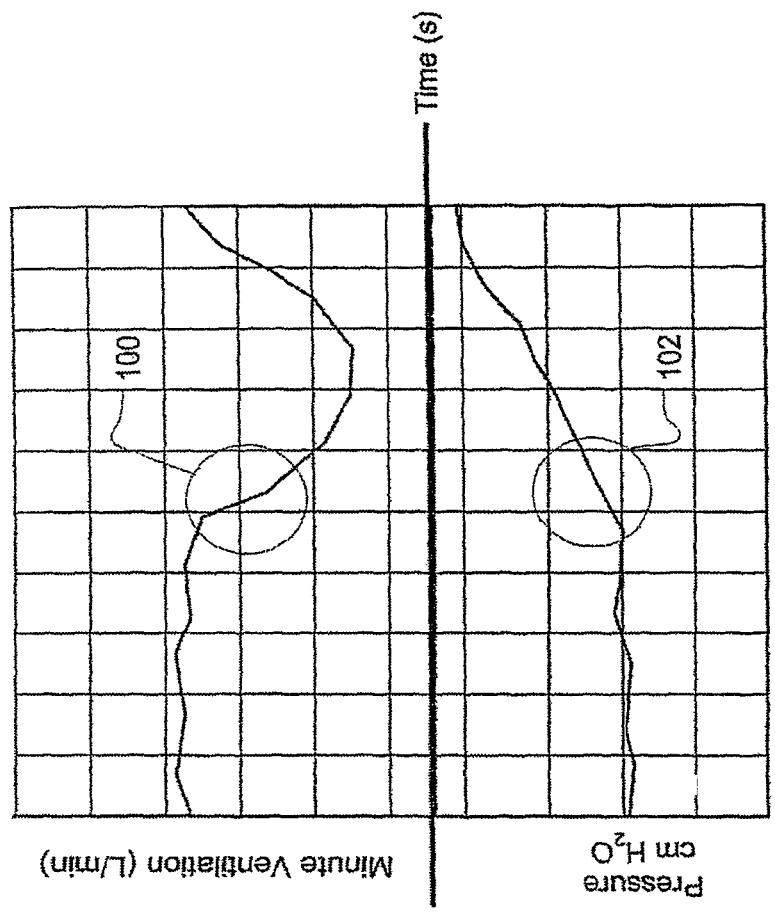
FIG. 10 illustrates a method of detecting obstruction from a measure of pressure and ventilation.

An alternative method for determining the existence of obstructive events involves an analysis of the relationship between a measure of ventilation and changes in pressure support. For example, if a measure of minute ventilation does not increase or remains the same when support pressure is increased, this would indicate that the patient is experiencing an obstructive event. Thus, the failure of the measure of ventilation to increase in relation to increases in pressure support would tend to indicate that the patient's airway is obstructed. In such a methodology, the measure of minute ventilation is monitored to detect a decrease in the minute ventilation. When pressure ventilation is increased to compensate for the decrease in the measure of minute ventilation, if the measure of minute ventilation does not increase in this general time frame, the device interprets the condition as detecting an incident of obstruction. This method is illustrated in the graphs of FIG. 10. The graphs plot a continuously determined minute ventilation (e.g., the volume of air inspired by the patient during the previous 60 seconds) and pressure delivered at the mask with respect to a common time scale. An obstructive event is determined when, after a decrease in minute ventilation shown at 100, there is no increase in minute ventilation corresponding to an increase in pressure 102. While the graph illustrates the method during delivery of a relatively constant CPAP pressure, those skilled in the art will recognize that the method may be accomplished in the presence of bi-level treatment or other pressure support which synchronizes smooth and comfortable pressure changes with the patients respiratory cycle by monitoring changes in end expiratory pressure.

Heart failure patients suffering from Cheyne-Stokes breathing are likely to suffer from reflex vocal cord closure in the initial stages of sleep when PCO2 in the blood is low, approximately between 5 and 30 minutes into sleep. As stable sleep is entered and partial pressure of carbon dioxide (PCO2) increases, the likelihood of these events diminishes. Vocal cord closure may generally be considered an obstructive event that may be detected in the manner that upper airway occlusions at the level of the tongue or soft palate are detected. Existing methods of obstruction detection as previously mentioned will detect both upper airway collapse and vocal cord closure but they cannot distinguish between these events. Due to the dangerous and counter-productive levels of pressure that would be required to open vocal cord closure (about 60 to 70 cm $H_2O$ or higher), the vocal cord event preferably is not treated like that of typical obstructive apneas, i.e., by increasing pressure, such as the end expiratory pressure, until the obstruction is opened. While vocal cord events may be treated by the same levels of pressure as other obstructive events, the treatment levels would not likely open the closure. Rather, such treatment is only likely to disturb the patient's sleep and prevent development of more stable deeper sleep. For these reasons, no increase in the treatment of reflex vocal cord closure is preferred.

Figure 2:
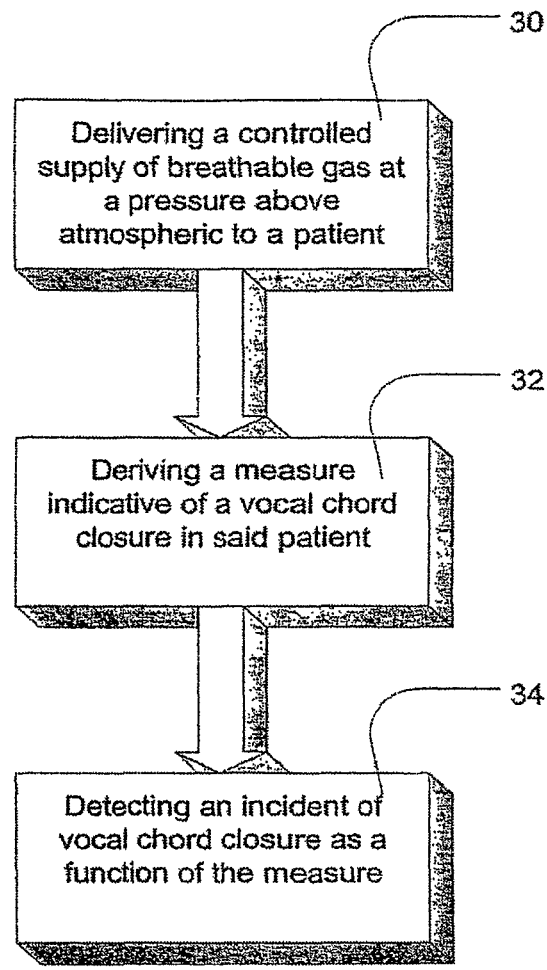
FIG. 2 is a flow chart of an embodiment of the invention for detecting vocal cord closure.

Accordingly, in determining the appropriate treatment protocol, a device of the invention preferably estimates or approximates whether the patient is awake or asleep, e.g., in some stage of sleep, and thus distinguishes between vocal cord closure and more typical obstructive events associated with sleep apnea. General steps in such a methodology are summarized in the flow chart of FIG. 2. In a delivering step 30, a controlled supply of breathable gas at a pressure above atmospheric is supplied to the patient. In a deriving step 32, a flow derived measure indicative of a vocal cord closure in a patient is determined. In a detecting step 34, an incident of vocal cord closure is detected as a function of the indicator.

Figure 3:
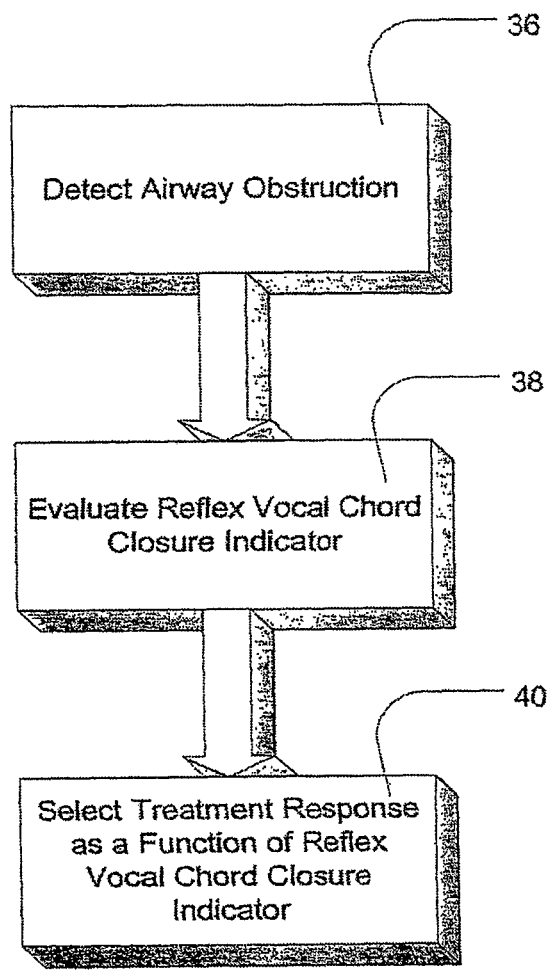
FIG. 3 is a flow chart of an embodiment of the invention for delivering treatment based on the detection of vocal cord closure.

With such an indicator, the device then selects between different treatment regimes. For example, initially, Cheyne-Stokes breathing and central apneas are treated while the patient is awake or in the early stages of sleep by delivering variations in pressure in phase with patient respiration to meet a target ventilation. During this treatment period obstructive events are ignored. Alternatively, obstructive events may be detected by observing an absence of or substantial decrease in airflow but those obstructions that are likely to be vocal cord closure are preferably not treated according to the indicator. After satisfying a threshold comparison with the indicator, subsequent obstructive events that are detected will be treated by an increase in pressure, such as, by increasing end expiratory pressure. Such a methodology is illustrated in the flow chart of FIG. 3. In a detection step 36, airway obstruction is detected. In an evaluation step 38, an indicator of vocal cord closure is determined. Finally, in a treatment step 40, treatment is determined as a function of the indicator. If vocal cord closure is detected then pressure is maintained at the current level or decreased. If vocal cord closure is not detected then pressure is increased as in the case of a typical obstruction. Appropriate pressure responses to typical obstructive events is described in more detail in U.S. Pat. No. 5,704,345.

One such indicator relates to a measure of ventilation, for example, a minute ventilation, i.e., the volume of measured airflow over the course of a minute. When a ventilation measure falls below a certain threshold, the indicator may suggest that the patient is in a later stage of sleep. To this extent, it will serve as an indicator to distinguish between obstructive events of vocal cord closure as opposed to tongue and soft palate closure. For example, if the minute ventilation, preferably averaged over a period of time, e.g., five minutes, is in a range of about 5 to 10 liters per minute, the patient is likely in a later stage of sleep. The accuracy of the indicator may be improved by making the threshold determination an additional function of time. For example, if the measure of ventilation is below a certain level and a period of time has elapsed, such as about 30 minutes, the patient is more likely to be in a later stage of sleep. In the preferred embodiment, if the mask has been on the patient for more than about 30 minutes and the minute ventilation averaged over a period of about five minutes is less than about 12 liters per minute, a later stage of sleep is indicated. This would also indicate that any detected obstructive events are of the more typical upper airway collapse of traditional obstructive sleep apnea rather than reflex vocal cord closure.

Another alternative indicator may be based upon the pressure swing. Swing is the difference between inspiration and expiration pressure levels as delivered by the apparatus in keeping with the effort of the patient's respiratory cycle. Typically, pressure swing is in the range of about 3 to 10 cm $H_2O$. Higher pressure swings in the range near about 10 cm $H_2O$ may be indicative of Cheyne-Stokes breathing. Thus, if swing is lower than that range for a period of time, e.g. about ten minutes, it would tend to indicate that the patient has settled into a later stage of sleep. Therefore, as the swing stabilizes, i.e., approaches a threshold, for example, about 8 cm $H_2O$ or less, and maintains that threshold for a certain time, the swing will be indicative of a later stage of sleep.

In a more simplified embodiment, a measure of time may serve to detect vocal cord closure by distinguishing between obstructive apneas and vocal cord closure based on this measure. In this embodiment, any detected obstructive events prior to the expiration of a period of time are considered to be vocal cord closure and not treated. For example, for any obstructive event detected before expiration of a time period of about 30 minutes from some start event, such as the initiation of a treatment session (e.g., when the machine is turned on or when the mask pressure first raises above ambient pressure) or by some other resetting or starting of a timer, these detected events would be considered vocal cord closure. Those events that are detected after expiration of the time period would then be considered treatable upper airway obstruction. In view of the preference to treat upper airway obstruction, rather than vocal cord closure, an alternative methodology may simply abstain from detecting obstructive events prior to the expiration of the time period. In this methodology, all events after the expiration of the time period are determined to be treatable upper airway obstructive events.

A preferred treatment protocol for responding to obstructive events in a manner that distinguishes between upper airway obstructive events and vocal cord closure is illustrated in FIG. 9. During a period of early sleep, e.g. about 30 minutes from starting use of the apparatus, obstructive events detected by any method are determined to be vocal cord closure. No increase in pressure from an initial pressure setting is permitted. During the latter stages of sleep, e.g. after about 30 minutes, detected obstructive events are treated by a step up in end expiratory pressure (EEP), for example, about 1-2 cm $H_2O$, which may be fixed or user selectable. Optionally, additional increases in pressure for detected obstructive events may be limited by the expiration of additional time periods. For example, a subsequent step in the EEP upon detection of another obstructive event would not be permitted until after about 10 minutes. Furthermore, increases in the EEP would not be permitted beyond a maximum pressure level. In the preferred embodiment, the initial EEP pressure is 5 cm $H_2O$ and increases in pressure step about 2 cm $H_2O$ and these steps are permitted after about 30 minutes have elapsed from the time that the patient has begun using the mask. Additional steps are permitted at about ten minute intervals thereafter. The limitation imposed by the additional intervals can be phased out after a sufficient time has elapsed which will substantially suggest that the patient is fully asleep, e.g., after about 1 to 2 hours of sleep, preferably after 100 minutes.

While vocal cord closure may also be determined by an insertable camera proximate to the patient's vocal cords, due to issues of comfort and equipment cost it is preferred to determine an indicator of closure as described above from a measure of respiratory airflow as a function of time. Of course, additional indicators may be based upon sleep data from EEG signals (electroencephalography) and/or EOG signals (electro-oculographic) or any other equipment used to determine sleep. Those skilled in the art would understand the nature of data from these devices for the purpose of distinguishing between the various stages of sleep that a subject will experience.

B. Positive Pressure Dose Measure

In order to manage administration of the treatment of the heart in the presence of positive pressure, for example, by delivering bilevel CPAP treatment, the preferred device calculates an index that represents the dose of treatment for the heart. With such a dose index, a physician may prescribe a certain quantity of treatment. Compliance then can be monitored by the pressure treatment apparatus so that the physician and patient can be certain that a treatment regimen is being satisfied.

Figure 11:
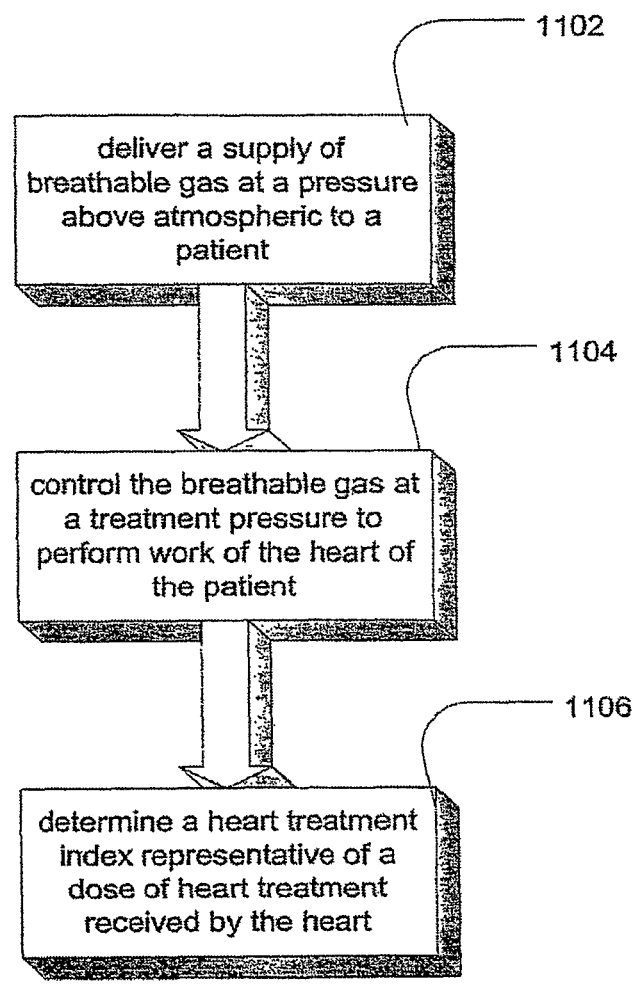
FIG. 11 is a flow chart illustrating steps in a methodology for determining a positive pressure dose measure of the invention.

Steps in such a methodology are illustrated in the flow chart of FIG. 11. In a delivery step 1102, a supply of breathable gas is delivered at a pressure above atmospheric to the airway of the patient. In a control step 1104, the pressure is controlled to perform work of the heart of the patient. In a determination step 1106, a heart treatment index representative of a dose of heart treatment experienced by the patient's heart is determined.

It is desirable to have such an index as a function of time and a function of pressure to assess the number of pressure hours received by the patient. Thus, the index may be viewed as having a pressure component and a time component. The preferred pressure component of the index is an average value of the pressure. Thus, the average pressure taken over the time period of treatment multiplied by the length of the time period can serve as a measure of dose. For example, if the average pressure delivered to the patient during a 5 hour treatment period is 7 cm $H_2O$, the dose is 35 cm $H_2O$-hours. In this embodiment of the does index, higher treatment pressures are weighted more than lower treatment pressures for purposes of determining compliance. Thus, a patient receiving an average 9 cm $H_2O$ of support pressure would satisfy the 35 cm $H_2O$-hours dose in approximately 3.9 hours.

Due to the breathing patterns experienced by CHF patients (i.e., Cheyne-Stokes breathing, partial obstruction, etc.) and the likely swings in pressure that are a result of treatment of such events, the index may be derived as the root mean square value of the pressure delivered during the treatment period. Such an index will more accurately provide an indicator of the pressure delivered given the pressure swings when compared with, for example, a median pressure.

With regard to the time component of the index, since CHF patients are likely to experience airway obstruction either due to a typical obstructive apnea or reflex vocal cord closure, the total time duration that the device delivers pressure support is not necessarily sufficient to accurately measure the treatment actually experienced by a subject's heart. Rather, it is preferred to consider the time period during which pressure is actually delivered to the thorax by excluding periods of closed airway obstruction. To this end, the preferred heart failure treatment dose index is a measure of delivered pressure during a time period that excludes duration of obstructive apneas and reflex vocal cord closures.

Accordingly, in the preferred embodiment, the dose index is a product of the average of the delivered pressure and an estimate of the number of hours that pressure is delivered to the thorax. Thus, the total number of hours of machine use is reduced to exclude the total time associated with airway obstructive events as these events are detected during treatment. For this purpose, the device quantifies periods of detected obstruction from the start of each obstruction through a point when the obstruction is alleviated. For example, an obstruction timer may commence when an obstructive apnea is detected if a calculated airflow variance falls below a threshold value. The obstruction timer will continue to track time until the calculated variance rises again above the threshold value. Of course, the time of the event may be excluded if it is determined to be a central apnea since the thorax will still be treated during a central apnea. Those skilled in the art will recognize other methods for quantifying the time period of the obstructive events that prevent pressure treatment of the thorax. Similarly, during the period of obstructive apnea, the determination of the average pressure may be suspended so that the pressure readings during this period do not affect the average pressure calculation.

Optionally, time periods of high or significant mask leak may similarly be excluded from the computation of thorax treatment time and average pressure. Such periods may be considered ineffective treatment. For example, the volume of measured airflow taken over a single breath cycle may be compared to a threshold value to determine if significant or high leak exists. Thus, the time period from such a comparison indicating high leak until the time that the comparison no longer indicated high leak could be excluded from the total treatment time and average pressure calculation. Those skilled in the art will recognize other methods for detecting leak for purpose of excluding periods of leak from the dose computation.

With such a device, treatment can be prescribed and delivered based on the dose index. For example, a pressure treatment device may optionally be implemented to accept as input a prescribed dose as a set-point index or prescribed threshold before use of the device. Then during treatment, the actual delivered dose is calculated and compared to the prescribed threshold to assess whether the actual delivered does satisfies the prescribed threshold. When the threshold is reached, the device may automatically cease delivery of pressure treatment. Preferably, the extent of the compliance with the prescribed dose may be recorded in the device for use by or transmission to the patient's physician. In one embodiment, the device may indicate that the dose has been achieved by generating a message, warning or alarm to the user or physician to advise the user that the dose has been reached and no further treatment is required.

C. Cardiac Pressure Oscillations

As previously noted, positive pressure can be applied to a subject's respiratory system to provide an oscillating force in the thorax proximate to the wall of the heart to assist with the work of the heart. To this end, positive pressure may be supplied to the subject's lungs to cause compression on the heart by increasing pressure during the systolic phase when the cardiac muscles contract. By reducing delivered pressure during the diastolic phase, treatment will more readily allow the cardiac muscles to relax.

Figure 4:
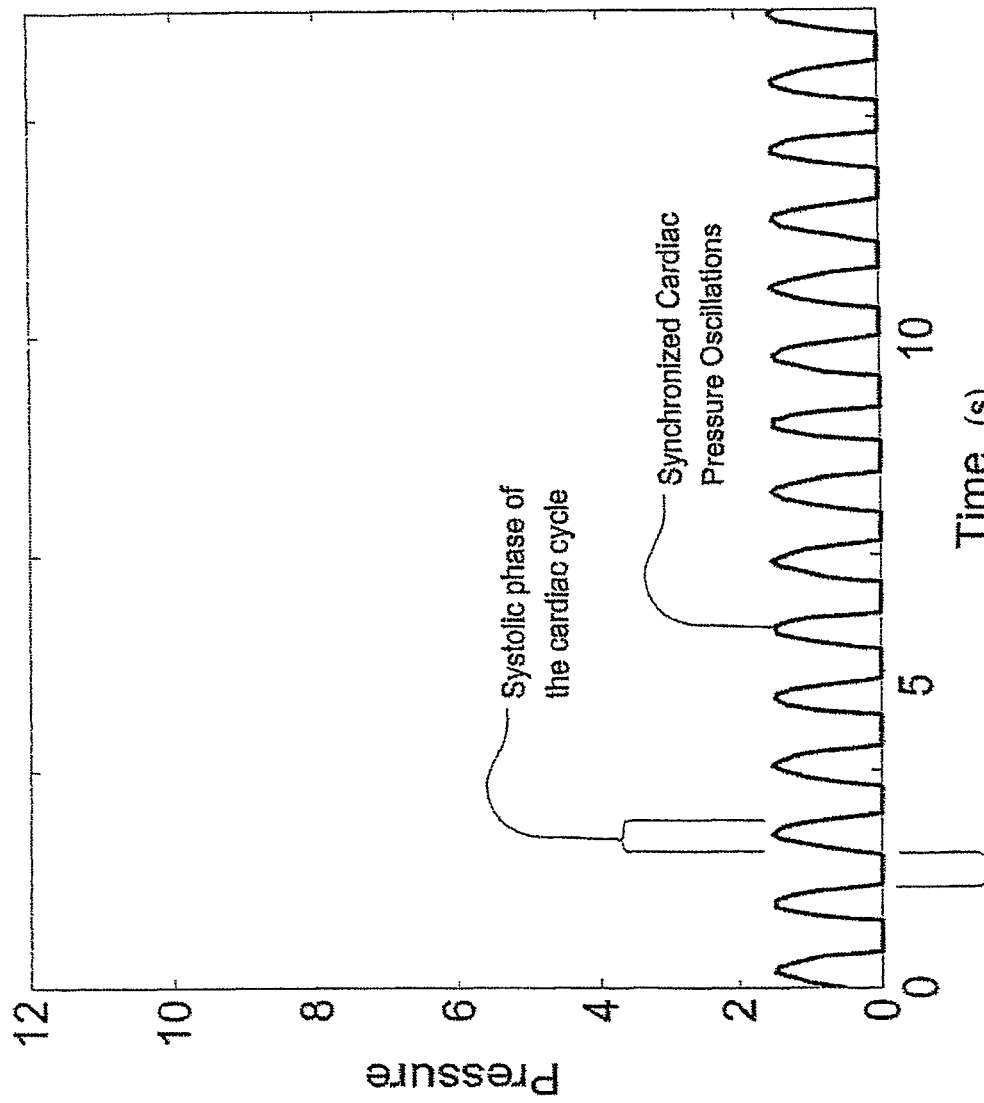
FIG. 4 is a graph of one form of a synchronized cardiac pressure oscillations in accordance with the invention.

These changes in pressure amplitude are chosen to have some effect on the heart without causing the subject discomfort. In the preferred embodiment, a cardiac pressure waveform with peak amplitude in the chosen range is superimposed on a level of positive pressure delivered in accordance with CPAP, hi-level pressure support or other pressure support variant such as the pressure delivered in accordance with a smooth pressure waveform template as disclosed in U.S. patent application Ser. No. 08/935,785. The cardiac treatment pressure waveform cycles to increase and decrease in phase with the cycle of the heart. One such synchronized cardiac waveform is illustrated in FIG. 4. Preferably, the peak pressure amplitudes associated with the systolic phase are in a range of about 1 to 4 cm $H_2O$. Although FIG. 4 depicts a clipped sinusoidal waveform, other waveform shapes may be used. For example, an oscillatory square wave may also serve to provide support for the contractions of the heart.

In order to synchronize the oscillations, the device determines the phase of the heart and triggers the cardiac pressure oscillations. In the preferred embodiment, cardiac rhythm is detected from an output signal from either an electrocardiogram (ECG) or a set of electrodes. Such electrodes each include a signal wire from the device which is attached to a metallic or otherwise conductive skin contact that can detect an electric charge. Electrical current generated by the heart in a person's chest flows to the surface and at the skin produces differences in electrical voltage which can be measured between pairs of electrodes placed at two points on the skin. Data from such electrodes is analyzed to time the delivery of each increase in pressure to generate the cardiac pressure waveform. Alternatively, cardiac rhythm may be determined from an airflow signal as described in U.S. Pat. No. 5,704,345 or otherwise estimated from the patient's pulse by an automated pulse rate detector on the wrist or finger of the patient.

Figure 5:
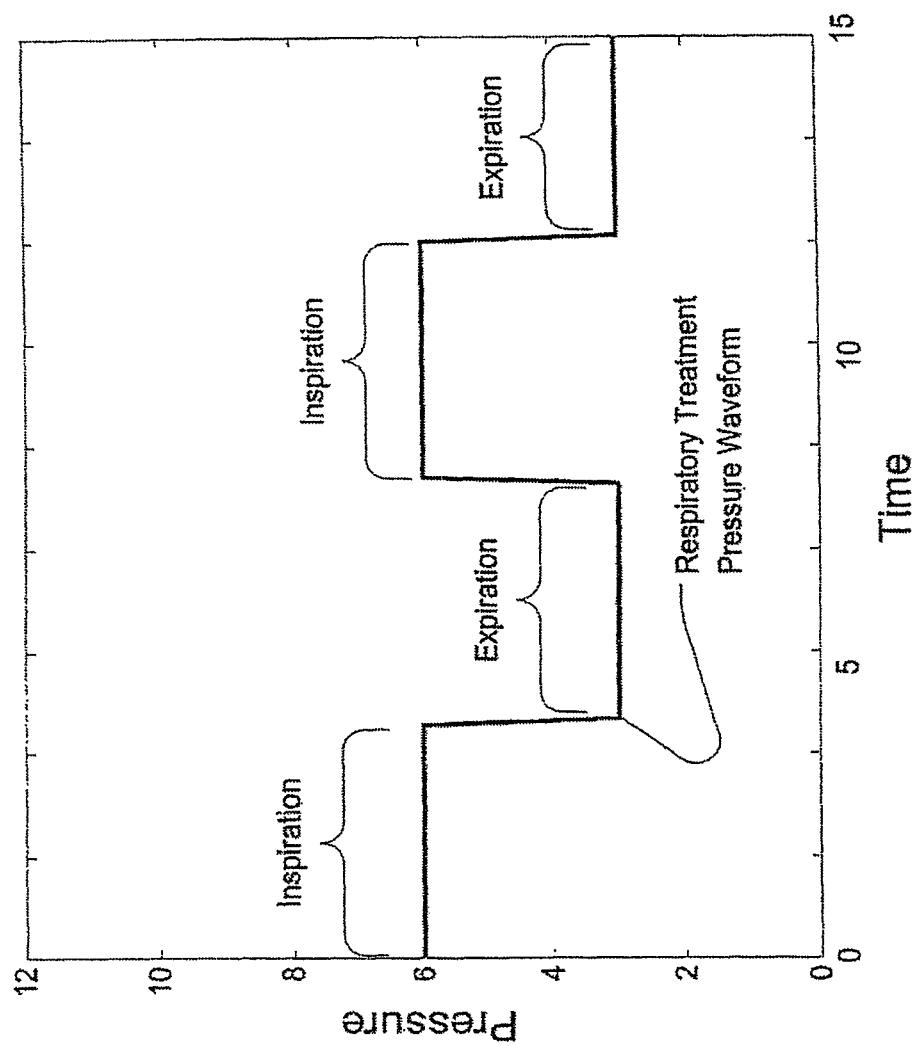
FIG. 5 is a graph of a respiratory treatment pressure waveform in accordance with the invention.
Figure 6:
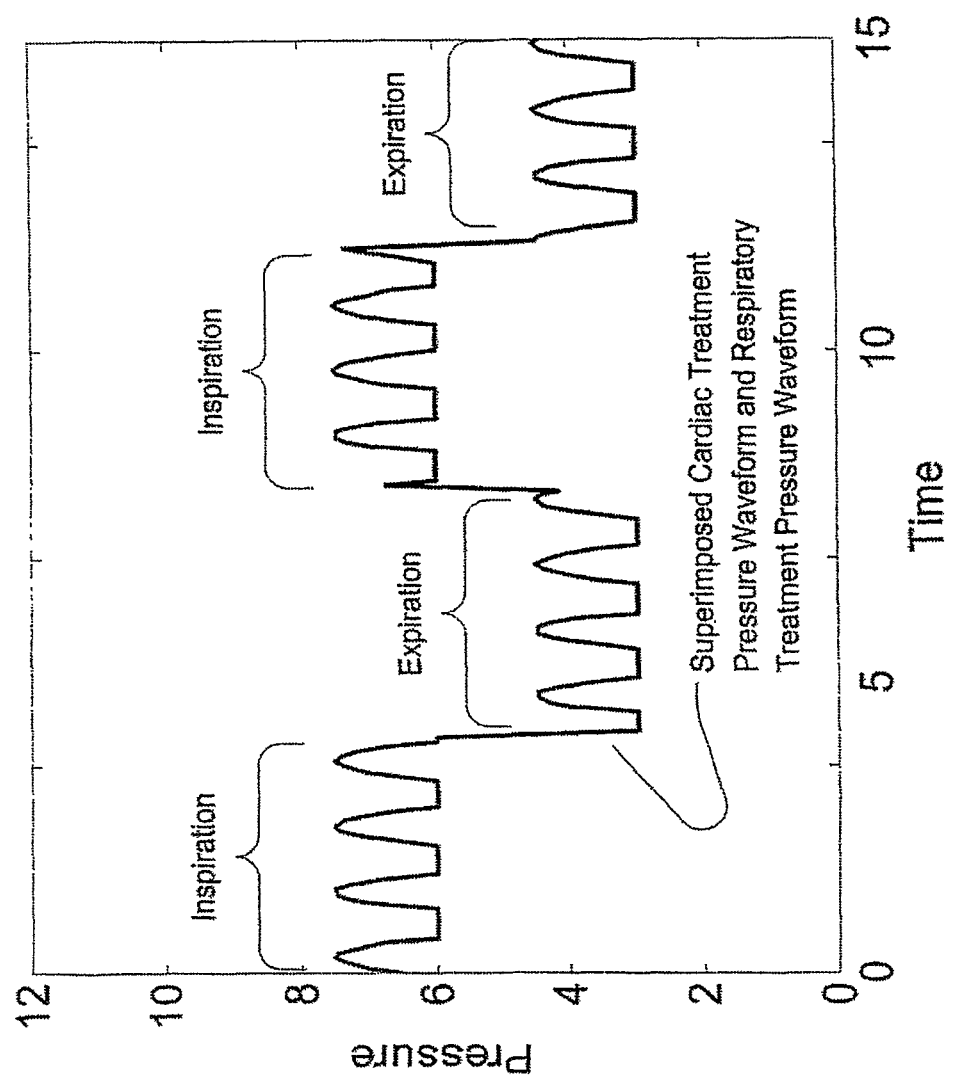
FIG. 6 is a graph of superimposed cardiac pressure oscillations with respiratory treatment pressure.

An example of the superposition of a cardiac pressure waveform and a respiratory pressure level or waveform is illustrated with reference to FIGS. 4, 5 and 6. The waveform shown in FIG. 5 depicts a hypothetical hi-level respiratory treatment pressure waveform with an IPAP generated for the inspiratory portions of a subject's respiratory cycle and an EPAP generated for the expiratory portions of the subject's respiratory cycle. The waveform depicted in the graph of FIG. 6 illustrates the superposition of the synchronized cardiac treatment pressure waveform of FIG. 4 with the respiratory treatment pressure waveform of FIG. 5.

D. Congestive Heart Failure Indicator

Another difficulty involving the treatment of heart failure patients relates to disease management. There are currently no known methods for accurately and continuously assessing a degree of severity or a degree of change in the patient's condition to assist care providers in predicting whether the patient is improving or not in response to a particular treatment regime. For example, when a physician treats heart failure with a particular drug, there is often insufficient information concerning whether the prescribed dose is particularly effective for the patient.

Accordingly, the preferred device determines or calculates one or more heart failure indicators or indices to indicate a change in heart failure condition or to rate a degree of severity of the heart failure condition. The changing value of such an indicator or index may provide a diagnostic tool for the physician to assess the state of the patient's health. For example, the indicator may provide information to inform the physician that the dosage of pharmacological agents given to the patient ought to be changed. If the index indicates that heart failure was stabilizing then it may be appropriate to reduce or maintain the dosage in use. Optionally, in accordance with an assessment of the heart failure indicator in which the indicator suggests that the patient is destabilizing, the device may begin to provide a specific dose of superimposed cardiac oscillations to perform some work of the patient's heart as previously described.

Alternatively, the index may be used to monitor the efficacy or effectiveness of a drug protocol. For example, the index may be monitored for a group of patients. This may include the storing of multiple indices in a database of patient information. By an analysis of such data, it may be determined that a drug is safe and/or appropriate as a treatment for heart failure in general.

Moreover, an index determined in accordance with the invention may be used by a physician in conjunction with other known methods of analyzing the health of the patient. For example, an index or indicator in accordance with the invention may be used in conjunction with changes in weight, medication dosage or lung fluid levels to detect changes in a subject's condition. Such an index may also be part of a battery of indicators for diagnosing whether or not a patient is suffering from heart failure in the first instance. For example, levels of B Natriuretic Peptide (BNP), a protein present in the blood that is secreted by heart muscle that is failing, which may be determined by a blood test and recorded by the apparatus and associated with the periods of use of the device as well as the indicators determined by the device.

Optionally, the apparatus prompts for input from a user so that the user can enter weight changes medication dosage, number of apneas or hypopneas, or other heart failure monitoring characteristics, such as levels of BNP. Thus, the device also serves as a database for recording heart failure monitoring characteristics. The device then may periodically transmit such data relating to the patient's condition to a centralized system for physician analysis. Alternatively, transmissions of such data may be performed on physician prescribed times or intervals or based on certain event criteria being met, such as a transmission trigger based upon recorded data meeting certain thresholds (e.g., the total number of apneas or hypopneas exceeding a certain threshold level or a change in a heart failure indicator compared with prior indices.)

The heart failure indices are determined from an analysis of the patient's breathing characteristics or by the machines' responses to the patient's breathing patterns. The indices may be determined in conjunction with a protocol for delivering treatment pressure or without such treatment pressure, for example, by simply monitoring patient respiratory airflow. Such indices serve as heart failure indicators to show patient improvement or relapse as detailed below. Such indicators may be recorded over various sessions with the device. In subsequent sessions, a current indicator or an average of such indicators may be compared with an indicator or average of such indicators from one or more prior sessions to analyze changes in the indicators.

Figure 12:
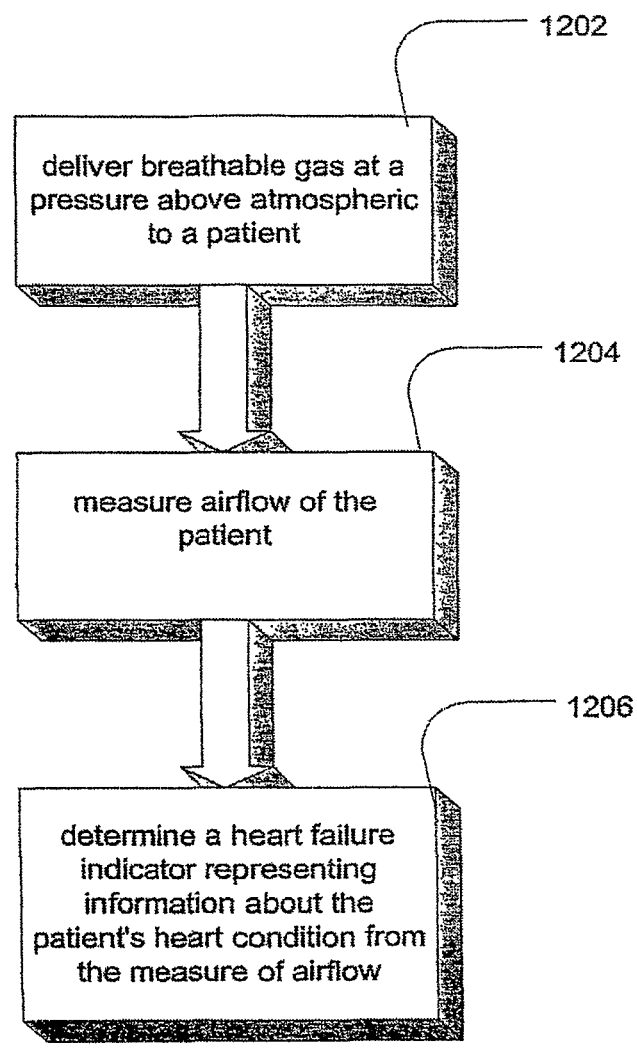
FIG. 12 is a flow chart illustrating steps in a methodology for determining a heart failure indicator or index.

Steps in such a methodology for evaluating heart failure in a patient are illustrated in the flow chart of FIG. 12. In a delivery step 1202, breathable gas is delivered to the patient at a pressure above atmospheric. In a measuring step 1204, the respiratory airflow of the patient is measured. In a determining or calculating step 1206, a heart failure indicator representing information about the patient's heart condition is derived from the respiratory airflow.

One such index is based upon a measure of the extent of the subject's Cheyne-Stokes breathing or a so-called "Cheyne-Stokiness" of the patient. As previously described, heart failure patients typically experience periods of the waxing and waning defined as Cheyne-Stokes breathing. The cycle of the waxing and waning typically will vary in the range of about 30 to 90 seconds, or even as high as 120 seconds. By examining variations or changes in the cycle, such as periodicity, it can serve as an indicator of the degree of severity or change in heart failure condition.

For example, by measuring the number Cheyne-Stokes cycles and determining increases or decreases in this number. Alternatively, the envelope period or duration of each waxing and waning cycle may be measured and compared to the time for one or more previous cycles or an average of prior cycles. A decrease may suggest that the patient's heart failure condition is improving. Similarly, an increase may suggest that the patient's heart failure condition is destabilizing. Thus, a current cycle time would be compared to a threshold, e.g., based on previously determined cycle times. Alternatively, the difference between current and prior measurements or a ratio of current and prior measurement may also serve as such an indicator.

One method for determining the duration of Cheyne-Stokes breathing is to determine the start time of a hyperapnea or hyperventilation and the end time of a subsequent apnea or hypopnea as shown in respiratory graph 70 of FIG. 7. In one embodiment, the start of the cycle may be indicated by an increase in a short-term measure of ventilation, for example, an instantaneous ventilation or a volume of airflow measured over a period of several seconds or less. Alternatively, it may be determined from an increase in peak values of airflow. The duration would then include the time period of the increase, the time period of a subsequent decrease in the short-term ventilation measure or decrease in peak airflow, and may include the duration of a possible period of cessation of airflow. Other methods for detecting each of these events, i.e., hyperapnea or hyperventilation, hypopnea and central apnea, are known in the art.

Alternatively, taking into account the nature of Cheyne-Stokes breathing, duration may be determined by identifying a particular point in one cycle and the similar point in the subsequent cycle. One such method involves a measure of instantaneous ventilation and a measure of recent average ventilation as disclosed in U.S. patent application Ser. No. 09/316,432. By monitoring a measure of instantaneous ventilation relative to a measure of recent average ventilation or target based on the average ventilation measure, an estimate of cycle time for Cheyne-Stokes breathing may be determined. For example, by monitoring the intersections of an instantaneous ventilation and an average ventilation and determining the time between two similar intersections or otherwise measuring the time between two such intersections, the duration of a Cheyne-Stokes cycle may be estimated. This method is illustrated in FIG. 7. The figure shows three graphs. The first graph of respiratory airflow depicts a number of cycles of Cheyne-Stokes breathing. The second graph shows a plot of one instantaneous ventilation (Instantaneous Ventilation 1) as measured in accordance with U.S. patent application Ser. No. 09/316,432. The third graph is a plot of another measure of instantaneous ventilation (Instantaneous Ventilation 2). As shown, the duration of the Cheyne-Stokes cycle on the respiratory graph 70 may be determined by measuring the duration on the ventilation graph 72. Thus, a timer may be reset to zero at the moment instantaneous ventilation changes from less than to greater than the recent average ventilation and the time elapsed is assessed when that condition is again true. Alternatively, the time of these points may be recorded and cycle time may be derived by calculation to determine the difference between the recorded times.

In another embodiment, the heart failure indicator may be an indication of Cheyne-stokes breathing determined from an average of a flow signal adjusted to remove leak. For example, if a measure of ventilation which, for preference, is an average minute ventilation or inspired volume over a one minute period, exceeds about 15 L/min, it is likely that the patient is experiencing an episode of Cheyne-Stokes breathing. The total number of these events can be logged. The changing value of such a heart failure indicators or indices may provide a diagnostic tool for the physician to assess the state of the patient condition. Thus, the information may be recorded over several sessions and increases or decreases in this number or durations from prior sessions, or averages from prior sessions, may then be determined, recorded and transmitted to the physician for review and analysis.

In one embodiment, the heart failure indicator may be a measure of ventilation variability. Such a measure may be a ratio of a maximum and minimum of a measure of ventilation. In patients experiencing Cheyne-Stokes breathing, a measure of minute ventilation will vary from a low of about 0 L/min to a high of about 25 L/min. For non-Cheyne Stokes breathing, patients typically will only experience changes in minute ventilation in a range of about 4 to 8 L/min. Accordingly, a heart failure indicator may be the ratio of the minimum to the maximum, preferably, as follows:

Heart Failure Indicator=Minimum(Ventilation)/Maximum(Ventilation)

Figure 8B:
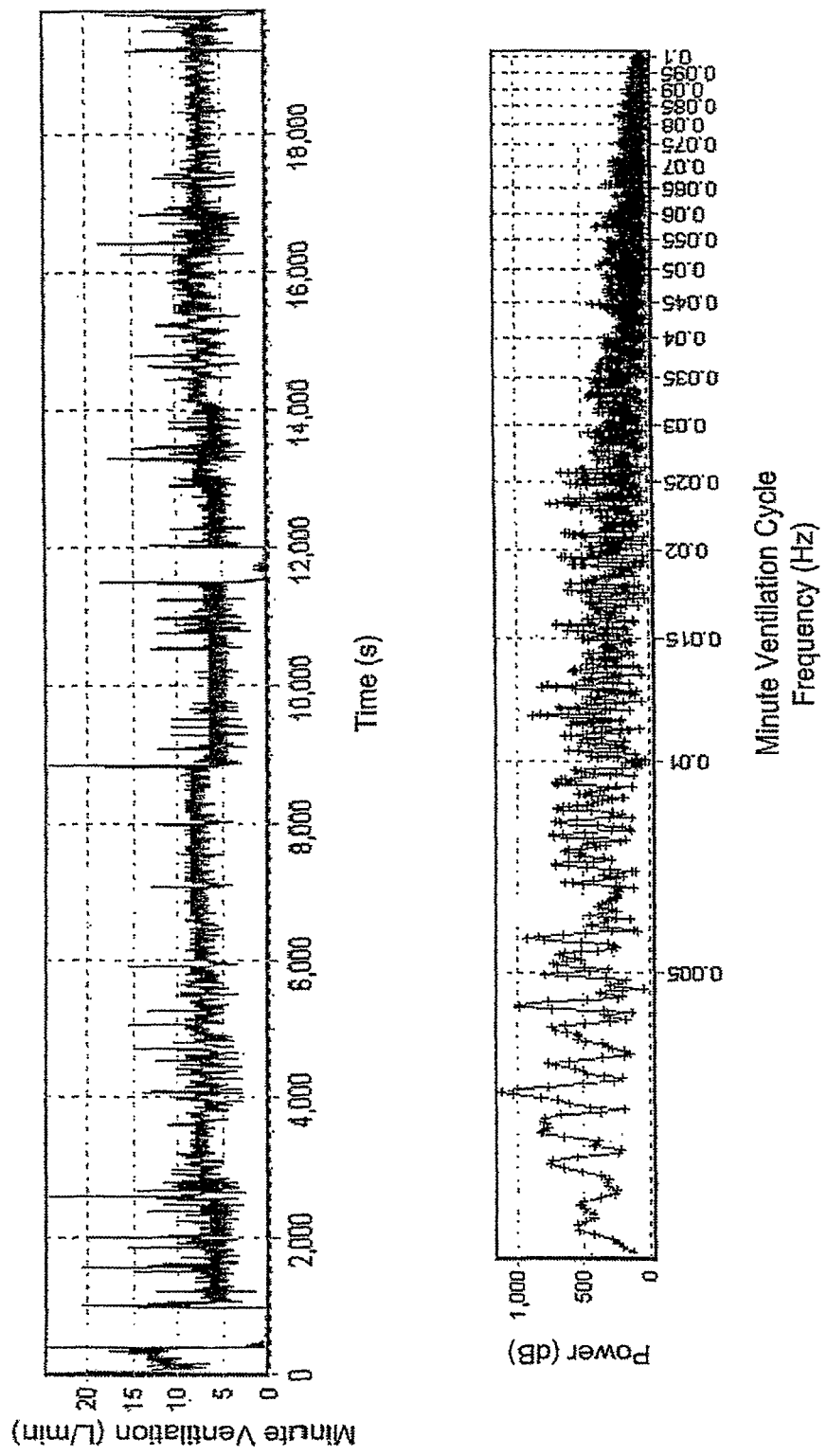
FIG. 8B depicts a graph of minute ventilation from a patient experiencing normal breathing and a graph of a frequency spectrum from the minute ventilation.

Notably, as the minimum measure of ventilation may be near 0, it is preferred that the minimum be divided by the maximum to avoid a divide by zero operation. Moreover, as an alternative, the indicator may be based on the ratio of minimum and maximum tidal volumes (i.e., a measure of ventilation of the patient taken during the inspiratory portion of a respiratory cycle.) For patients experiencing Cheyne-Stokes breathing, the tidal ventilation may vary from 0 up to 1.5 or as much as 2.5 liters. Another method for determining an appropriate heart failure indicator, which is intended to assess the extent of Cheyne-Stokes breathing, is to measure a volume of airflow, e.g., a minute ventilation or a filtered measure of airflow with a time constant of about 10 seconds, and record the resulting waveform or sampled data representing the waveform over time. At the conclusion of a period of measurement, such as one treatment episode or various intervals during one such episode, the data or waveform is analyzed to isolate the frequencies typically associated with Cheyne-Stokes waxing and waning periods. This frequency analysis involves a Fourier Transform such as a DFT or FFT to examine a frequency range of about $5 \times 10^{-2}$ Hz to $1.1 \times 10^{-2}$ Hz since the period for a typical Cheyne-Stokes cycle is in the range of about 20 to 90 seconds in duration. With such an analysis preferably with emphasis in a sub-range of $\frac{1}{30}$ Hz to $\frac{1}{60}$ Hz, a quantitative measure of the extent of Cheyne-Stokes breathing may be extracted. Since normal patient respiratory cycles would be reflected at much higher frequencies, the chosen range would be indicative of Cheyne-Stokes cycles. An example of a frequency spectrum 80 is shown in FIG. 8A, depicting a frequency analysis of components of a measure of airflow in the range of frequencies generally associated with Cheyne-Stokes breathing. The bottom graph of FIG. 8A illustrates the existence of Cheyne-Stokes breathing in the minute ventilation signal of the top graph of FIG. 8A. The bottom graph of FIG. 8B illustrates the lack of Cheyne-Stokes breathing in the minute ventilation signal of the top graph of FIG. 8B.

By observing different distributions or different spreads at different peaks in the band or by comparing shifting frequency bands in the frequency range of interest over different periods, changes in the resultant frequency spectrum will indicate changes in Cheyne-Stokes breathing. Thus, an embodiment of the invention quantifies components in the range of Cheyne-Stokes frequencies as one or more indices and/or generates a visual frequency spectrum of the Cheyne-Stokes frequencies to show a graphical pattern of the patient's Cheyne-Stokes breathing. Such indicators may be based upon analyses or quantifications of the spectrum that include a determination of a total power, for example, a sum of amplitudes or magnitudes of components at all frequencies in the entire band of frequencies or a portion thereof, a determination of magnitudes or a measure of a peak value at one or more separate frequencies, a determination of a measure of central tendency or standard deviation, or similar.

By monitoring changes in the resulting quantification and/or pattern shifts the indicators may then serve as indicators of a change in heart failure condition. For example, if the magnitudes or patterns indicate that the patient's Chenye-Stokes breathing is increasing in duration, becoming more frequent or otherwise increasing in intensity, it may indicate that the patient's heart failure condition is destabilizing and a different treatment approach (medicinal or otherwise) to the patient's condition may be warranted. Alternatively, a decrease in the duration, frequency or intensity of such breathing may indicate that the current treatment approach is appropriate. Thus, these quantifications (e.g., duration, a magnitude, sum of magnitudes, or standard deviation) derived during a current session may be compared to a threshold value. The threshold may be a predetermined acceptable level or a quantification derived from a previous analysis in a current session or from a previous treatment session with the device.

In one embodiment of the device based upon an analysis of any of the various indicators previously mentioned or as a function of a change in such indicators, a warning such as an audible alarm or other visual signal is generated or this information may be transmitted to a system for access by a physician. For example, if the current heart failure indicator including a duration is greater than a prior indicator or a desired threshold of change in the indicator, a warning is generated. The alarm or warning is intended to alert a care provider or user to the potential destabilization of the patient if a change in the indicator suggests such destabilization. Alternatively, indicators may be recorded over time to provide long-term statistical analysis of the patient's condition subsequent to treatment with the device. For example, such indicators may be recorded over various sessions with the device in a database or other information storage medium.

In one embodiment of the invention, the device may respond to the onset of one or more periods of Cheyne-Stokes breathing by reducing pressure support to permit data from a Cheyne-Stokes breathing event to be recorded in the absence any significant treatment pressure that might impact or change the nature of the pattern of breathing. For example, if a Cheyne-Stokes breathing event is detected, the amplitude of pressure support may be reduced by about 50% for a particular period of time, for example, about 10 minutes, so that data during the event may be recorded. A limit on the number of these untreated data collection sessions may also be implemented so that the patient's Cheyne-Stokes breathing does not go completely untreated during any treatment session with the apparatus. For example, the device may record data for three Cheyne-Stokes events during any single treatment session. This reduced treatment data collection process may be performed consecutively for each consecutively detected Cheyne-Stokes event up to the optional limit. Alternatively, a certain number of detected Cheyne-Stokes events, one or more, may be fully treated by an appropriate support pressure response before a subsequently detected event will be evaluated in a reduced treatment data collection process. Thus, a full treatment process and reduced treatment data collection process may alternate over a number of detected Cheyne-Stokes events.

In addition to providing a measure for a qualitative analysis of the patient's heart failure condition, the indicator may be utilized as an input to an automated pressure adjustment algorithm that can serve to provide additional treatment for the heart. For example, the indicator may be utilized to increase end expiratory pressure. In one embodiment, when the minute ventilation exceeds a 15 L/min threshold, the pressure may be increased by a small quantity, for example about 1 cm $H_2O$. Optionally, any additional changes to the treatment pressure based on the indicator would not take place until expiration of a predetermined time period, such as about 10 minutes.

Similarly, in the case of the indicator that is determined as a ratio of minimum and maximum ventilation measures, based on a comparison of the indicator with a threshold value, the pressure may be increased by a small degree, e.g., about 1 cm $H_2O$. For example, the pressure may be increased as follows: If MIN(tidal volume)/MAX(tidal volume)<a threshold in a range of about 0.04 to 0.25, preferably about 0.1 to 0.2, for example, about 0.15, after a period of about 10 minutes then increase the pressure by about 1 cm $H_2O$.

The aforementioned indicators or the measures on which they are based may be filtered with a time constant of about 5 or 10 minutes. Such an operation permits the filtering out of the consequences of short term changes in these continuously determined measures.

While the invention has been described with various alternative embodiments and features, it is to be understood that the embodiments and features are merely illustrative of the principles of the invention. Those skilled in the art would understand that other variations can be made without departing with the spirit and scope of the invention as defined by the claims.

Where ever it is used, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

It will be understood that the invention disclosed and defined herein extends to all alternative combinations of two or more of the individual features mentioned or evident from the text or drawings. All of these different combinations constitute various alternative aspects of the invention.

The invention claimed is:

1. A method for evaluating heart failure in a patient comprising steps of:
   delivering, by a blower, breathable gas at a pressure above atmospheric to a patient;
   detecting, by a controller, obstructive events experienced by the patient;
   varying, by the blower, the pressure of the breathable gas responsive to obstructive events detected by the controller;
   determining a heart failure indicator from machine responses to the patient's breathing patterns, said machine responses comprising said responsive pressure variations, said heart failure indicator representing information about the patient's heart condition; and comparing said heart failure indicator to a prior heart failure indicator determined during a previous treatment session, wherein said heart failure indicator is analysed to determine a change in said heart failure indicator over time, wherein said change is a difference between said prior heart failure indicator of said previous treatment session and said heart failure indicator.

2. The method of claim 1, further comprising measuring an airflow of the patient, wherein said step of determining includes analyzing said airflow to determine an extent of Cheyne-Stokes breathing of the patient.

3. The method of claim 2 further comprising the step of reducing said pressure during a detected episode of Cheyne-Stokes breathing for a predetermined period of time to permit a determination of said heart failure indicator from said predetermined period of time such that a pattern of Cheyne-Stokes breathing can emerge without significant influence from treatment pressure.

4. The method of claim 2 wherein said step of determining includes analyzing said airflow to determine a duration of a waxing and waning cycle.

5. The method of claim 2 wherein said step of determining includes a frequency analysis of said airflow in a range of frequencies indicative of Cheyne-Stokes breathing.

6. The method of claim 5 wherein said frequency analysis of said airflow is in a range of about 1/20 hertz to 1/90 hertz.

7. The method of claim 6 wherein said heart failure indicator includes a magnitude of a component of said airflow at a frequency in said range.

8. The method of claim 7 wherein said heart failure indicator is a sum of magnitudes of components of said airflow in a sub-range of frequencies in said range.

9. The method of claim 5 wherein said frequency analysis of said airflow is performed with data sampled from a measure of ventilation derived from said airflow.

10. The method of claim 9 wherein said measure of ventilation is a minute volume.

11. The method of claim 7 further comprising a step of comparing said magnitude with a threshold value.

12. The method of claim 11 wherein said threshold value is a magnitude derived from a previous frequency analysis.

13. The method of claim 1 further comprising steps of prompting for heart failure monitoring characteristics and recording said heart failure monitoring characteristics and said heart failure indicator in a database.

14. The method of claim 13 wherein one of said heart failure monitoring characteristics is a level of B natriuretic peptide.

15. The method of claim 1 further comprising a step of identifying subsequent heart failure treatment based at least in part upon said heart failure indicator.

16. The method of claim 15 wherein said subsequent heart failure treatment is an increase in pressure of the breathable gas.

17. The method of claim 1 further comprising the step of analyzing said heart failure indicator as a function of a threshold value.

18. The method of claim 1 wherein said indicator is a function of a measure of ventilation.

19. The method of claim 1 further comprising determining a change that is a ratio of a previous heart failure indicator and a subsequent heart failure indicator.

20. The method of claim 1 further comprising a step of generating a warning as a function of said change from said step of analyzing.

21. The method of claim 20 wherein said warning is an audible alarm.

22. The method of claim 1 wherein said indicator is a measure of ventilation.

23. The method of claim 22 wherein said measure of ventilation is a threshold of about 15 L/min.

24. The method of claim 1 wherein said indicator is a ratio of a minimum ventilation and a maximum ventilation.

25. The method of claim 24 wherein the minimum ventilation and maximum ventilation are derived from a measure of minute ventilation.

26. The method of claim 24 wherein the minimum ventilation and maximum ventilation are derived from a measure of tidal volume.

27. An apparatus for evaluation of heart failure in a patient comprising:

a blower for supplying breathable gas to a patient at a pressure above atmospheric; and a controller adapted and configured to:

detect obstructive events experienced by the patient;

control said blower such that the pressure varies responsive to detected obstructive events;

determine a heart failure indicator from machine responses to the patient's breathing patterns, said machine responses comprising said responsive pressure variations, said heart failure indicator representing information about the patient's heart condition; and compare said heart failure indicator to a prior heart failure indicator determined during a previous treatment session, wherein the controller determines a change in said heart failure indicator over time, wherein said change is a difference between said prior heart failure indicator of said previous treatment session and said heart failure indicator.

28. The apparatus of claim 27 further comprising a flow sensor to generate a flow signal indicative of the patient's airflow, wherein the determining includes analyzing said flow signal to determine an extent of Cheyne-Stokes breathing of the patient.

29. The apparatus of claim 28 wherein the controller is further configured and adapted to reduce said pressure during a detected episode of Cheyne-Stokes breathing for a predetermined period of time to permit a determination of said heart failure indicator from said predetermined period of time such that a pattern of Cheyne-Stokes breathing can emerge without significant influence from treatment pressure.

30. The apparatus of claim 28 wherein the determining comprises analyzing said flow signal to determine a duration of a waxing and waning cycle.

31. The apparatus of claim 28 wherein the determining comprises a frequency analysis of said flow signal in a range of frequencies indicative of Cheyne-Stokes breathing cycle.

32. The apparatus of claim 31 wherein said frequency analysis of said flow signal is in a range of about 1/20 hertz to 1/90 hertz.

33. The apparatus of claim 32 wherein said heart failure indicator includes a magnitude of a component of said flow signal at a frequency in said range.

34. The apparatus of claim 33 wherein said heart failure indicator is a sum of magnitudes of components of said flow signal in a sub-range of frequencies in said range.

35. The apparatus of claim 31 wherein said frequency analysis of said flow signal is performed with data sampled from a measure of ventilation derived from said flow signal.

36. The apparatus of claim 35 wherein said measure of ventilation is a minute volume.

37. The apparatus of claim 33 wherein the controller is further configured and adapted to compare said magnitude with a threshold value.

38. The apparatus of claim 37 wherein said threshold value is a magnitude derived from a previous frequency analysis.

39. The apparatus of claim 27 wherein the controller is further configured and adapted to prompt for heart failure monitoring characteristics and recording said heart failure monitoring characteristics and said heart failure indicator in a memory.

40. The apparatus of claim 39 wherein one of said heart failure monitoring characteristics is a level of B natriuretic peptide.

41. The apparatus of claim 27 wherein the controller is further configured and adapted to control a step of identifying subsequent heart failure treatment based at least in part upon said heart failure indicator.

42. The apparatus of claim 41 wherein said subsequent heart failure treatment is an increase in the pressure of the breathable gas.

43. The apparatus of claim 27 wherein said controller is further configured and adapted to analyze said heart failure indicator as a function of a threshold value.

44. The apparatus of claim 27 wherein said indicator is a function of a measure of ventilation.

45. The apparatus of claim 27 wherein the controller is adapted and configured to determine a change that is a ratio of a previous heart failure indicator and a subsequent heart failure indicator.

46. The apparatus of claim 27 wherein said controller is further configured and adapted to generate a warning signal as a function of said change from said step of analyzing.

47. The apparatus of claim 46 wherein said warning signal triggers an audible alarm in said apparatus.

48. The apparatus of claim 27 wherein said indicator is a measure of ventilation.

49. The apparatus of claim 48 wherein said measure of ventilation is a threshold of about 15 L/min.

50. The apparatus of claim 27 wherein said indicator is a ratio of a minimum ventilation and a maximum ventilation.

51. The apparatus of claim 50 wherein the minimum ventilation and maximum ventilation are derived from a measure of minute ventilation.

52. The apparatus of claim 50 wherein the minimum ventilation and maximum ventilation are derived from a measure of tidal volume.

\* \* \* \* \*